United States Patent [19]
Marlow et al.

[11] Patent Number: 5,571,137
[45] Date of Patent: *Nov. 5, 1996

[54] ENDOSCOPIC INSTRUMENT SYSTEM AND METHOD

[75] Inventors: Scott C. Marlow, Chesterland; Haans K. Petruschke, Kirtland; Donald B. Coon, Chesterland; John T. Nelson, Kirtland, all of Ohio

[73] Assignee: Marlow Surgical Technologies, Inc., Willoughby, Ohio

[*] Notice: The term of this patent shall not extend beyond the expiration date of Pat. No. 5,368,606.

[21] Appl. No.: 292,094

[22] Filed: Aug. 17, 1994

Related U.S. Application Data

[62] Division of Ser. No. 907,853, Jul. 2, 1992, Pat. No. 5,368,606.
[51] Int. Cl.⁶ .................................................. A61B 17/28
[52] U.S. Cl. ........................... 606/207; 606/167; 606/205
[58] Field of Search ............................ 606/1, 110, 113, 606/79, 139, 151, 213, 205–211, 167, 170, 171, 176; 128/749–754, 898, 20

[56] References Cited

U.S. PATENT DOCUMENTS

| | | | |
|---|---|---|---|
| 1,127,948 | 2/1915 | Wappler | 606/170 |
| 1,274,669 | 8/1918 | Bohn . | |
| 2,113,246 | 4/1938 | Wappler . | |
| 2,114,695 | 4/1938 | Anderson . | |
| 2,790,437 | 4/1957 | Moore . | |
| 3,837,345 | 9/1974 | Matar . | |
| 4,084,594 | 4/1978 | Mosior . | |
| 4,122,856 | 10/1978 | Mosior et al. . | |
| 4,258,716 | 3/1981 | Sutherland . | |
| 4,569,131 | 2/1986 | Falk et al. . | |
| 4,646,751 | 3/1987 | Maslanka . | |
| 4,721,116 | 1/1988 | Schintgen et al. . | |
| 4,971,067 | 11/1990 | Boldue et al. . | |
| 5,026,375 | 6/1991 | Linovitz et al. | 606/79 |
| 5,053,043 | 10/1991 | Gottesman . | |
| 5,133,735 | 7/1992 | Slater et al. . | |
| 5,147,357 | 9/1992 | Rose et al. . | |
| 5,147,373 | 9/1992 | Ferzli . | |
| 5,172,700 | 12/1992 | Bencini et al. . | |
| 5,234,460 | 8/1993 | Stouder | 606/205 |
| 5,269,785 | 12/1993 | Bonutti | 606/167 |
| 5,282,806 | 2/1994 | Haber et al. | 606/207 |
| 5,304,203 | 4/1994 | Mallawany et al. | 606/207 |
| 5,308,358 | 5/1994 | Bond et al. | 606/207 |
| 5,320,635 | 6/1994 | Smith | 606/170 |
| 5,368,606 | 11/1994 | Marlow et al. | 606/170 |

FOREIGN PATENT DOCUMENTS

| | | |
|---|---|---|
| 1089924 | 9/1960 | Germany . |
| 9007356 | 5/1991 | Germany . |
| 2140735 | 12/1984 | United Kingdom . |
| 9102493 | 3/1991 | WIPO . |
| 9217116 | 10/1992 | WIPO . |

*Primary Examiner*—Glenn Dawson
*Attorney, Agent, or Firm*—Thompson Hine & Flory

[57] ABSTRACT

An endoscopic instrument system which includes a handle portion with a scissors grip, a shaft extending from the scissors grip and shaped to extend through a cannula, and a plurality of disposable end tools, each mountable on the end of the shaft and actuatable by the scissors handle. In a preferred embodiment, the scissors handle actuates a rod extending through the shaft which is connected to the end tool. The end tool includes a pair of jaws pivotally mounted on the support and connected to a reciprocating stub shaft by links. The stub shaft is connected to the actuating rod of the handle portion so that movement of the scissors handle causes the jaws to pivot relative to each other. The end tool may take the form of a scissor, grasper, biopsy or dissector, depending upon the specific shape of the jaws. An advantage of the invention is that the support of the end tools is made of a relatively inexpensive plastic material such that the end tools may be discarded when the jaws become dull, thus obviating the need for repeated cleaning and sharpening and eliminating the most difficult portion to clean.

11 Claims, 2 Drawing Sheets

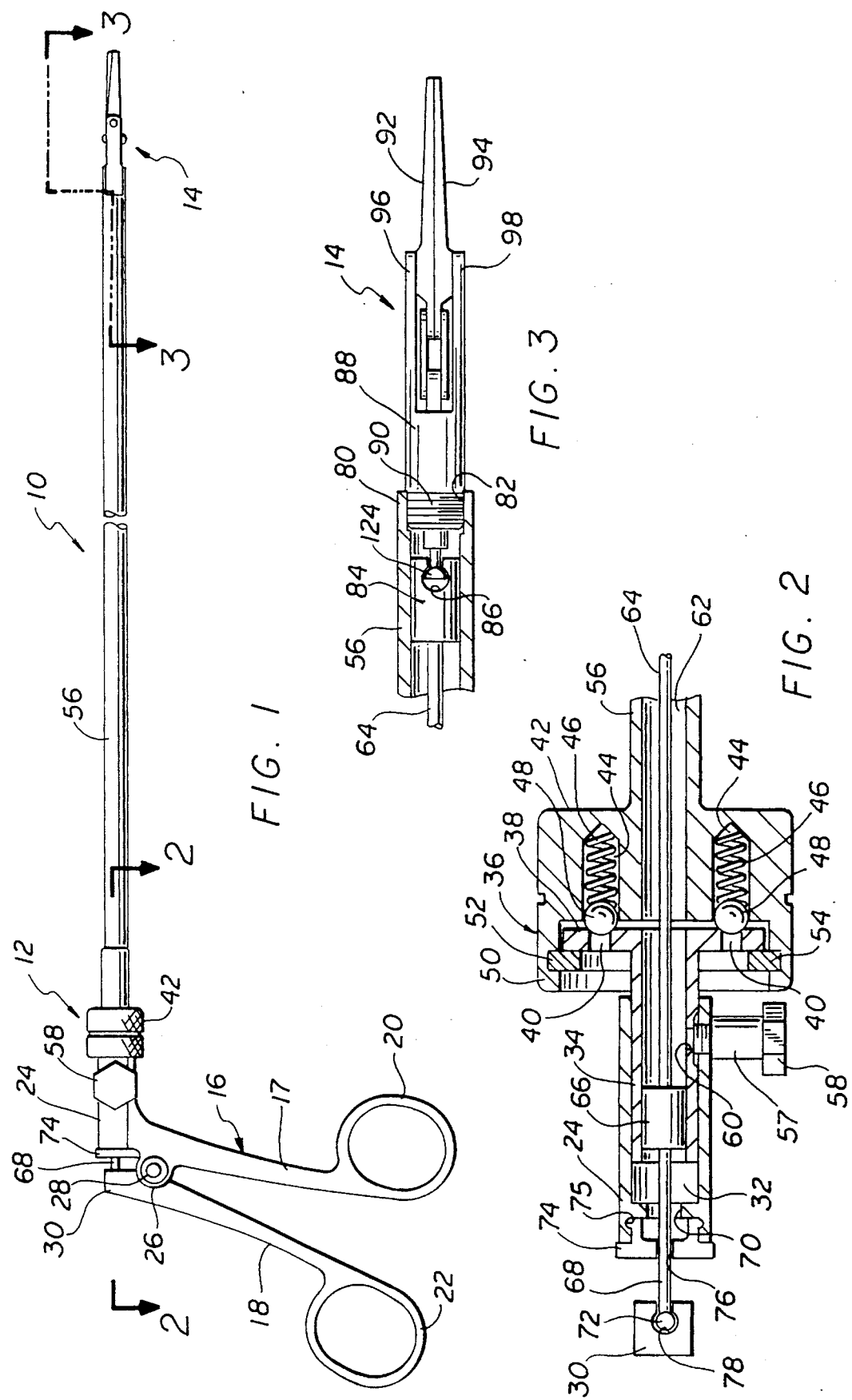

ENDOSCOPIC INSTRUMENT SYSTEM AND METHOD

This is a division of application Ser. No. 07/907,853 filed Jul. 2, 1992, now U.S. Pat. No. 5,368,606.

BACKGROUND OF THE INVENTION

The present invention relates to surgical instruments and, more particularly, to endoscopic instruments suitable for use with a trocar or cannula.

A branch a endoscopic surgery is laparoscopic surgery which involves the use of a cannula that is inserted through an incision in the skin of the subject to provide access to an internal cavity, such as the thoracic cavity. An example of such a cannula is disclosed in Hasson U.S. Pat. No. 5,002,557, the disclosure of which is incorporated herein by reference. Surgery is performed with a laparoscopic instrument, which typically includes a scissors handle and an elongate shaft terminating in a pair of pivoting jaws. The handle includes a scissors of pliers grip which, when squeezed and released, reciprocates a rod extending through the shaft to pivot the jaws. The jaws and shaft are sized to be inserted through the cannula into the body cavity where the surgery is to be performed. Similar devices are employed in thoroscopic and arthroscopic surgery.

As with any surgical instrument, should the tool include sharpened jaws for cutting, it is desirable to maintain the sharpened edges as sharp as possible for each operation. Further, it is also desirable to design the instrument so that it can be easily and thoroughly cleaned after each operation. However, disadvantage with unitary instruments; that is, instruments in which the handle, shaft and cutting tool are permanently attached to each other, is that cleaning of the instrument and sharpening of the tool after each operation becomes time-consuming and costly.

Accordingly, attempts have been made to provide laparoscopy instruments which minimize the time and expense of cleaning and sharpening. For example, some laparoscopy instruments are made in which substantially the entire instrument is constructed of plastic, except for the shaft rod and jaws, so that the entire instrument is disposable after each operation. Alternately, instruments such as those disclosed in Falk et al. U.S. Pat. No. 4,569,131 are designed in which the handle is separable from the shaft and jaws, so that the unitary shaft, jaws and rod may be disposed after each use, or cleaned and sharpened separately from the handle. A disadvantage with these types of designs is that the disposable component—whether it be the entire instrument or only the shaft and cutting tool— provides an undesirably high volume of medical waste which requires special disposal procedures. Further, disposable instruments made largely of plastic are somewhat flimsy and difficult to maneuver.

Accordingly, there is a need for a laparoscopy instrument which eliminates the need for repeated sharpening of the cutting surfaces of the instrument and which facilitates cleaning and reduces cross contamination potential.

SUMMARY OF THE INVENTION

The present invention is an endoscopic instrument system which includes a handle portion having a elongate shaft for insertion through a cannula and a plurality of end tools, each attachable to the end of the shaft. In the preferred embodiment, each of the end tools includes pivoting jaws which actually contact the tissue of the subject during the operation. The end tools preferably include plastic components which lower their cost, and are disposable. One advantage of the present invention is that the disposable component of the entire instrument is relatively small, thereby minimizing the cost of using the instrument over several operations and minimizing the volume of medical waste comprised by the disposable components of the instrument.

In a preferred embodiment, the handle portion includes pivoting scissor handles and an actuating rod which extends through the shaft. The rod terminates in a clevis which receives the hemispherical tip of a stub shaft that is reciprocatably mounted within the end tool. The stub shaft is connected to a pair of pivoting jaws by links so that reciprocal movement of the stub shaft causes the jaws to pivot relative to the end tool in a scissors fashion.

The end tool includes a support which is made of a glass fiber reinforced plastic and threads onto the open end of the handle shaft. The pivoting jaws of the end tools may be formed to perform a variety of tasks; for example, the jaws can be in the form of scissors, graspers, biopsy, or dissectors.

Another advantage of the present invention is that only the portions of the instrument which become most contaminated during an operation and are most difficult to clean; namely, the jaws and linkage operating the jaws are disposed of with the end tool. In the preferred embodiment, a cleaning port extends through the handle portion and facilitates the flushing of the shaft with an appropriate liquid cleaning agent after each operation. A direct result of incorporating the laparoscopy instrument of the present invention in a hospital operating room procedure is that a relatively few handle portions need be present while having a relatively large number of end tools, in contrast to prior procedures in which an extensive array of unitary instruments must be present. Further, each surgeon may be provided with a set of end tools, each performing a different function, and each selected from an array of end tools to suit the particular surgeon's needs and preferences.

Accordingly, it is an object of the present invention to provide an endoscopic instrument system which eliminates the need for repeatedly sharpening the cutting jaws of the instrument; an instrument system in which the linkage components which are the most difficult to clean are disposable, thereby obviating the necessity for repeated cleaning; an instrument system in which the shaft portion is easily cleaned after each operation; an instrument system in which the cutting surfaces and linkages are disposable such that the volume of disposed equipment is minimized; an instrument system having a disposable cutting element in which the support component is made of a relatively inexpensive plastic material; an instrument system having a plurality of attachable end tools which can be customized for a particular practitioner or application; and an instrument system which is relatively easy to manufacture and utilize.

Other objects and advantages of the present invention will be apparent from the following description, the accompanying drawing and the appended claims.

BRIEF DESCRIPTION OF THE DRAWING

FIG. 1 is a side elevation of the handle portion and one end tool of a preferred embodiment of the endoscopic instrument system of the present invention;

FIG. 2 is a section taken at line 2—2 of FIG. 1;

FIG. 3 is a section taken at line 3—3 of FIG. 1;

DETAILED DESCRIPTION

Figure 4:
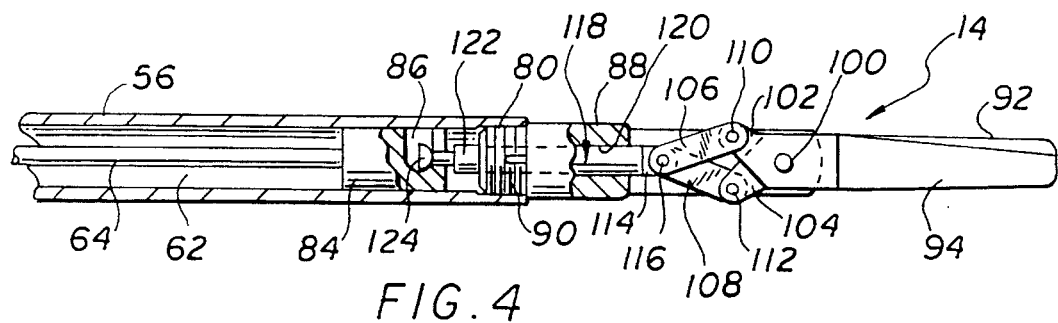
FIG. 4 is a detail of the instrument of FIG. 1 showing the shaft end in section and a portion of the end tool broken away.

As shown in FIG. 1, the endoscopic instrument system of the present invention, generally designated 10, includes a handle portion, generally designated 12, and an end tool, generally designated 14. The handle portion 12 includes a scissors component 17 which is gripped by the user and has front and rear scissors handles 17, 18, respectively. Scissors handles 17 and 18 include finger loops 20, 22.

Scissors handle 16 is attached to a cylindrical housing 24 and includes a clevis 26 which is engaged by scissors handle 18 and secured by a screw 28. When scissor handle 18 is pivoted relative to handle 16 about screw 28, the upper end 30 of handle 18 reciprocates relative to the housing 24.

As shown in FIG. 2, the housing 24 includes a hollow interior 32 which receives an inner sleeve 34 of a rotatable coupling 36. The inner sleeve 34 includes a flange 38 having a plurality of orifices 40 spaced about its periphery. The coupling 36 includes a coupling body 42 having a plurality of cylindrical cavities 44, each receiving an extension spring 46 which urges a ball 48 against an adjacent one of the orifices 40. The balls 48 are larger in diameter than the orifices so that the orifices merely provide seats for the balls 48. The inner end 50 of the coupling body 36 includes an annular groove 52 which receives a split ring 54. The split ring 54 retains the coupling body 42 on the flange 38. The body 42 is unitary with a hollow, elongate shaft 56 (see also FIG. 1). While the shaft 56 of the preferred embodiment is made of surgical stainless steel, it is within the scope of the invention to provide a flexible shaft.

The external surface of the body 42 is knurled to facilitate grasping by a user. The coupling 36 enables the shaft 56 to be rotated relative to the housing 24 of the handle portion 12, and the engagement of ball 48 and orifices 40 provide detent stops.

The housing portion 24 includes a lateral tube 57 which is capped by a removable nut 58 and communicates with the interior 32 of the housing. The tube 57 extends through an opening 60 in the sleeve 34 to communicate with the interior 62 of the coupling 36 and shaft 56.

The handle portion 12 includes a rod 64 which extends through the interiors 62, 32 of the shaft 56 and housing 24, respectively. The rod includes an enlarged, cylindrical segment 66 which engages the interior or internal wall of the sleeve 34 for location purposes and a rear segment 68 which protrudes through an end opening 70 in the housing 24 to terminate in a spherical end 72. The housing 24 includes a plastic end cap 74 mounted in a dovetail slot 75 which provides a seal about the extension 68. The extension 68 passes through an orifice 76 in the cap and the end 72 of the extension is received within a clevis 78 formed in the upper end 30 of the handle 18. Consequently, pivoting movement of the handle 18 relative to handle 16 causes the upper end 30 to reciprocate relative to the housing 24, causing the rod 64 to reciprocate relative to the handle portion 12.

As shown in FIG. 3, the outer end 80 of the shaft 56 includes a threaded interior surface 82. The end 84 of the rod 64 includes a clevis 86. The end tool 14 includes a support 88, preferably made of a glass filled plastic, such as 40% glass filled polyetherimide. Other plastics include polyethersulfone and polyetheretherketone. Support 88 has a threaded inner end 90 which is shaped to thread into the threaded interior 82 of the end 80 of shaft 56. The support 88 mounts a pair of jaws 92, 94, which are best shown in FIG. 4.

The support 88 includes a pair of arms 96, 98 (see FIG. 3) which receive a rivet 100 that mounts the jaws 92, 94 for pivotal movement relative to the support and to each other. The jaws 92, 94 each include ears 102, 104 which are pivotally attached to links 106, 108 by rivets 110, 112. The links 106, 108 are, in turn, pivotally attached to a knuckle 114 by a rivet 116. The knuckle 114 forms a portion of a stub shaft 118 which is slidably mounted within a passage 120 formed in the support 88. The stub shaft is sized such that an inner end 122 protrudes rearwardly from the threaded end 90 and terminates in a hemispherical tip 124 which is shaped to be seated within the clevis 86.

Figure 5:
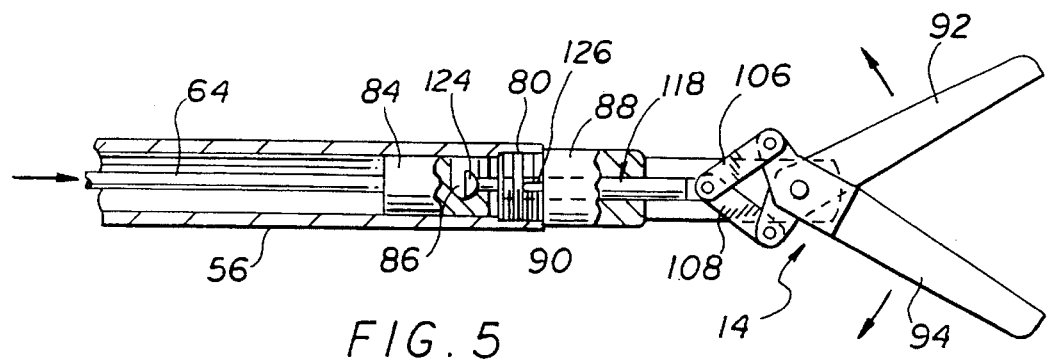
FIG. 5 is the detail of FIG. 4 in which the tool jaws have been pivoted to an open position.

As shown in FIG. 5, displacement of the rod 64 relative to the shaft 56 by pivoting the handle 17, 18 in the manner previously described causes the end 84 of the rod to displace the stub shaft 118 outwardly relative to the support 88. This outward displacement causes the links 106, 108 to pivot the jaws 92, 94 outwardly away from each other. Conversely, displacement of the rod 64 inwardly, causes by squeezing the handles 17, 18 together (see FIG. 1), causes the stub shaft 118 to be displaced inwardly relative to the support 88, so that the links 106, 108 draw the jaws 92, 94 together. Consequently, pivotal movement of handle 18 relative to handle 17 causes the jaws 92, 94 to pivot relative to each other.

To remove the end tool 14 from the shaft 56, the support 88 is first threaded out of the threaded end 80 of the shaft 56. The loops 20, 22 of the handles 17, 18 are drawn together, which displaces the rod end 84 outwardly from the shaft end 80, exposing the clevis 86. Once the rod end 84 clears the shaft end 80, the tip 124 of the stub shaft 118 can be removed from the clevis 86 and the entire end tool 14 discarded. It is not necessary to remove the rod 64 from the handle portion 12 or disconnect the extension 68 from the handle upper end 30.

Reattachment of a fresh end tool 14 is accomplished by reversing the aforementioned sequence of steps. Specifically, the fresh tool 14 is placed adjacent to the shaft end 80 and the tip 124 placed into the clevis 86. The handles 17, 18 are spread slightly and the support 88 is threaded into the shaft end 80. In the preferred embodiment, the threaded end 90 of the support 88 includes bosses 126 which are deformed by the threads of the threaded end 80 to prevent the inadvertent unthreading of the end tool 14.

To clean the handle portion 12 of the instrument system 10, the tip 14 is first removed as previously described. Then, the nut 58 is removed from the tube 57 and a cleaning solvent is flushed through the interiors 32, 62 of the housing 24 and shaft 56 so that the solvent exits the end 80 of the shaft, thereby flushing any debris from the shaft. However, it should be noted that the connection of the tip 14 with the shaft end 80 minimizes the entry of contaminants within the interior 62, since the only openings are the seam between the shaft end and support 88 and the passage 120 and stub shaft 118.

Figure 6:
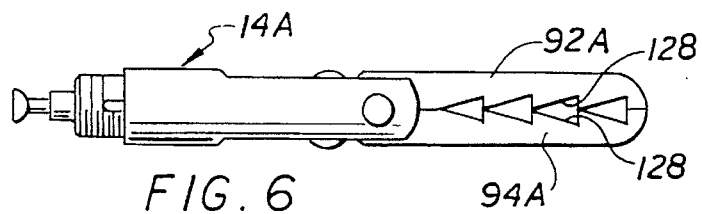
FIG. 6 is a side elevation of a gripper end tool of the present invention.
Figure 7:
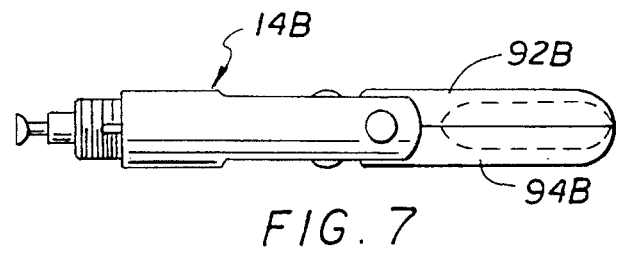
FIG. 7 is a side elevation of a biopsy end tool of the present invention.
Figure 8:
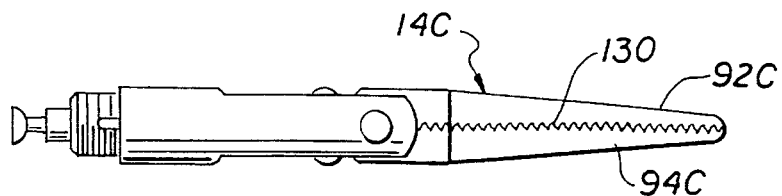
FIG. 8 is a side elevation of a dissector end tool of the present invention.

FIGS. 6, 7 and 8 show alternate embodiments of the end tool 14A, 14B, 14C, each designed to perform a specialized function and forming a component of the system 10. In 14A, the jaws 92A, 94A include rear-facing sawtooth edges 128 such that the tip 14A forms an alligator grasper. In FIG. 7, the end tool 14A includes jaws 92A, 94A which are shaped to form a biopsy. In FIG. 8, the end tool 14C includes jaws 92C, 94C having sawtooth edges 130 to form a dissector.

While the form of apparatus herein described constitute a preferred embodiment of the invention, it is to be understood that the invention is not limited to this precise form of apparatus, and that changes may be made therein without departing from the scope of the invention.

What is claimed is:

1. A method of using an endoscopic instrument system of a type having at least one endoscopic instrument and a plurality of disposable instrument end tools, each of said end tools having a support and at least one jaw and including linkages to effect movement of said jaw relative to said support comprising the steps of:

selecting one endoscopic instrument of a type having a handle portion including means for gripping said instrument, means forming a shaft extending from said gripping means and means for actuating said instrument;

selecting a single instrument end tool from the plurality of disposable end tools, said end tool being of a type having means for replaceably mounting said end tool on an end of said shaft and including at least one movable jaw, linkages to effect movement of said jaw and means for engaging said actuating means, whereby said at least one jaw of said end tool is operable relative to said support by said actuating means;

mounting said end tool on said shaft;

using said endoscopic instrument and said end tool; and subsequent to use of said instrument and end tool, removing said end tool with said support, said at least one jaw, said engaging means and said linkages from said shaft.

2. The method of claim 1 wherein said mounting step includes the step of attaching said actuating means to said end tool.

3. The method of claim 2 wherein said removing step includes the step of detaching said actuating means from said end tool.

4. The method of claim 1 wherein said removing step includes the step of disposing of said end tool.

5. The method of claim 1 further comprising the final steps of sterilizing said instrument; and repeating said instrument end tool selecting step and said instrument end tool mounting step.

6. The method of claim 1 wherein said instrument end tool selecting step comprises the step of selecting said single end tool from among a plurality of end tools of different configurations for performing different tasks.

7. A method of performing an operation using an endoscopic instrument system of a type having at least one endoscopic instrument and a plurality of disposable end tools, each of said end tools having a stub shaft extending from a proximal end thereof, comprising the steps of:

selecting one endoscopic instrument of a type having a handle portion including means for gripping said instrument, means forming a shaft extending from said gripping means and an actuator rod for actuating said instrument;

selecting a single instrument end tool of a type having means for replaceably mounting said end tool on an end of said shaft and including at least one moveable jaw and a stub shaft for engaging said actuator rod and actuating said jaw, said end tool being selected from among said plurality of end tools having different configurations for performing different tasks, whereby said end tool is operable by said actuator rod; and mounting said end tool on said shaft;

utilizing said tool in an operation; and removing said end tool with said movable jaw and said stub shaft from said shaft.

8. The method of claim 7 further comprising the step of subsequent to said removing step selecting a second end tool from said plurality of end tools and mounting said second end tool on said shaft.

9. The method of claim 8 further comprising the step of disposing of said removed end tool subsequent to said removing step and retaining said instrument for further use.

10. The method of claim 7 wherein said mounting step includes the step of attaching said actuator rod to said stub shaft of said end tool.

11. The method of claim 10 further comprising the step of removing said end tool from said shaft and detaching said end tool from said actuator rod subsequent to use of said instrument and end tool.

\* \* \* \* \*